United States Patent [19]

Baba

[11] Patent Number: 4,633,855
[45] Date of Patent: Jan. 6, 1987

[54] ENDOSCOPE APPARATUS

[75] Inventor: Kazuo Baba, Tokyo, Japan

[73] Assignee: Olympus Optical Co., Ltd., Tokyo, Japan

[21] Appl. No.: 782,145

[22] Filed: Sep. 30, 1985

Related U.S. Application Data

[63] Continuation of Ser. No. 683,949, Dec. 19, 1984, abandoned, which is a continuation of Ser. No. 512,314, Jul. 8, 1983, abandoned, which is a continuation of Ser. No. 295,704, Aug. 24, 1981, abandoned.

[30] Foreign Application Priority Data

Sep. 2, 1980 [JP] Japan ................... 55-121371

[51] Int. Cl.$^4$ .............................. A61B 1/06
[52] U.S. Cl. ...................................... 128/6
[58] Field of Search ....................... 128/4–9, 128/660; 350/20, 115, 116; 73/612

[56] References Cited

U.S. PATENT DOCUMENTS

| | | |
|---|---|---|
| 3,430,625 | 3/1969 | McLeod, Jr. . |
| 3,542,014 | 11/1970 | Peronneau . |
| 3,595,220 | 7/1971 | Kawahara . |
| 3,710,310 | 1/1973 | Moss . |
| 3,730,632 | 5/1973 | Chikama ................... 128/6 |
| 3,817,631 | 6/1974 | Kawahara . |
| 3,819,267 | 6/1974 | Kawahara . |
| 3,895,854 | 7/1975 | Ziffer ................... 350/20 |
| 3,964,297 | 6/1976 | Jorgensen et al. ............. 73/612 |
| 4,154,114 | 5/1979 | Katz et al. ................... 128/660 |
| 4,204,548 | 5/1980 | Kurz . |
| 4,271,829 | 6/1981 | Heckele ................... 128/6 |

FOREIGN PATENT DOCUMENTS 2950203  6/1980  Fed. Rep. of Germany .......... 128/4

OTHER PUBLICATIONS

"How Things Work", part 1, 1979, Granada, pp. 150-151, London, *Focal Distance and Size of Image.*

Primary Examiner—Edward M. Coven
Assistant Examiner—Max F. Hindenburg
Attorney, Agent, or Firm—Frishauf, Holtz, Goodman & Woodward

[57] ABSTRACT

An endoscope apparatus includes an ultrasonic transducer disposed at the distal end portion of an endoscope. The ultrasonic wave transmission/reception time of the ultrasonic transducer is measured by a time counter. The measured time from the time counter and the velocity of propagation of ultrasonic wave are operated on by a calculator to calculate the distance between the distal end portion and a subject. The distance and the view angle of an observation optical system are operated on by a calculator, the ratio between the size of an image in the field of view of the observation optical system and the size of the subject is calculated, and the scale of a scale display panel disposed inside the field of view of the optical system is indicated in accordance with such ratio. The graduations of the scale are variable as a function of said calculated ratio.

10 Claims, 6 Drawing Figures

ENDOSCOPE APPARATUS

This application is a continuation of application Ser. No. 683,949, filed Dec. 19, 1984 which in turn is a continuation of Ser. No. 512,314 filed July 8, 1983, which in turn is a continuation of Ser. No. 295,704 filed Aug. 24, 1981, all now abandoned.

BACKGROUND OF THE INVENTION

This invention relates to an endoscope apparatus, and more specifically to an endoscope apparatus capable of measuring the size of an affected part of a subject.

Conventionally, in observing the interior of a body cavity by means of an endoscope, the size of an affected part of a subject image observed within the field of view of an optical system for observation varies with the change of the distance between the objective lens of the endoscope and the subject. Namely, the affected part looks greater as the objective lens approaches closer to the affected part, whereas it looks smaller when the objective lens is far from the affected part. Thus, the actual size of the affected part cannot be measured from the image in the field of view. Accordingly, there have been proposed various expedients for measuring the actual dimensions of the affected part. Some of these expedients are as follows:

(1) A spot light is diagonally applied at a given angle to the optical axis of the objective lens, the distance between the position of the spot light in the field of view and the subject is measured, and the measured size of the affected part is calculated using the measured distance as a conversion factor for actual size.

(2) A flexible scale with graduations is inserted through a forceps channel to be held against the affected part, and is observed through the endoscope for reading.

(3) The moved distance of e.g. the objective lens moved for the focusing of the optical system for observation is measured, and the size of the affected part is calculated on the basis of the moved distance.

In conjunction with (1), however, the objective lens is wide-angled for ease of orientation in the body cavity, so that the aberration of the objective lens is too great for accurate measurement of the distance between the objective lens and the subject. In some cases, therefore, the measurement error may amount to 30% to 40%. The expedient (2) is not a perfect measure because the operation of holding the scale against the affected part is too hard a task to ensure quick measurement. In connection with (3), moreover, the depth of field of the optical system for observation is substantial because it cannot practically be reduced so much. Accordingly, even though the moved distance of the objective lens is detected, the measured value obtained will be subject to an error corresponding to such depth of field, and the size of the affected part will not be able to be measured with accuracy.

SUMMARY OF THE INVENTION

The object of this invention is to provide an endoscope apparatus capable of accurately measuring a lens-to-subject distance by means of ultrasonic waves, calculating the actual size of the subject on the basis of the measured distance and the view angle of an optical system for observation, and indicating the calculated value within the field of view of the optical system.

According to this invention, an ultrasonic transducer is disposed at the distal end of an endoscope, the time between transmission of ultrasonic waves from the ultrasonic transducer and reception of echo waves from the subject is measured, and the distance between the distal end and the subject is calculated as a function of the ultrasonic transmission/reception time. The actual size of the subject is calculated as a function of such calculated distance and the view angle of the optical system for observation, and is indicated on a sacle within the field of view of the optical system, the scale having variable graduations.

DETAILED DESCRIPTION OF THE PREFERRED EMBODIMENTS

Figure 1:
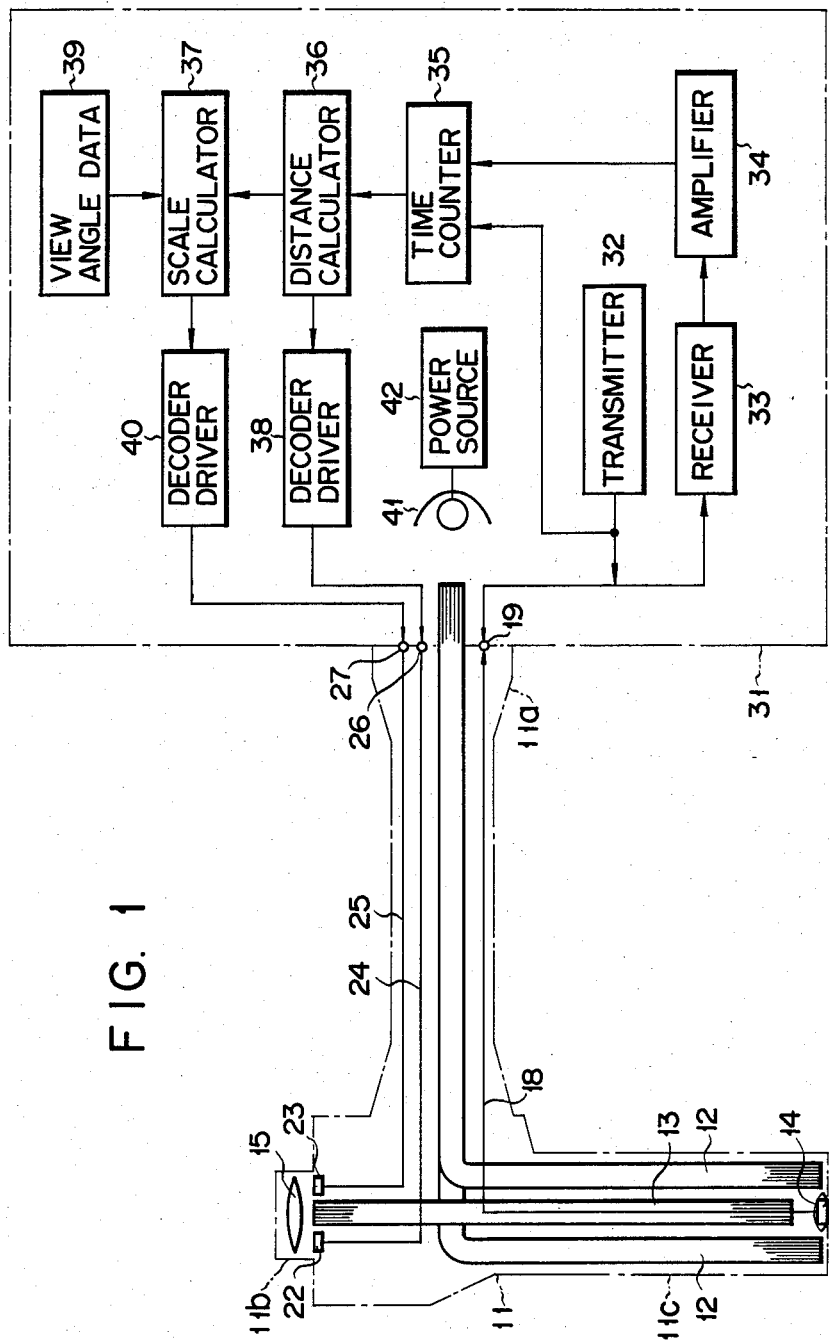
FIG. 1 is a schematic diagram of an endoscope apparatus according to an embodiment of this invention.
Figure 2:
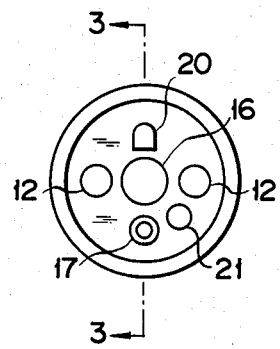
FIG. 2 is a plan view of the distal end portion of the endoscope apparatus.
Figure 3:
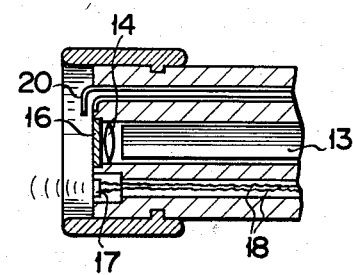
FIG. 3 is a sectional view taken along line 3—3 of FIG. 2.

Referring now to the drawing of FIG. 1, there is shown an endoscope 11 including an optical system for observation and a light guiding optical system for illumination which are provided with light guides 12, 12 and an image guide 13, respectively. An objective lens 14 and an eyepiece lens 15 are disposed on the front and rear ends of the image guide 13, respectively. As shown in FIGS. 2 and 3, an ultrasonic transducer 17 is disposed in the vicinity of an observation window 16. The ultrasonic transducer 17 is connected to the connector pin 19 of a connector 11a by means of a signal line 18. An air-water feed nozzle 20 is intended to clean the observation window 16, while a suction port 21 is provided for discharging air or water fed through the air-water feed nozzle 20.

Figure 4:
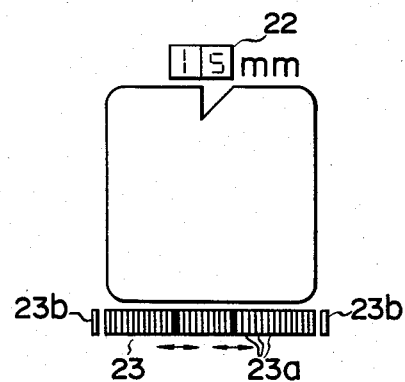
FIG. 4 shows a field of view of an optical system for observation.

At an eyepiece section 11b, as shown in FIGS. 1 and 4, a distance display panel 22 and a scale diplay panel 23 are disposed in close proximity to the rear end face of the image guide 13. The distance display panel 22 is formed of LED segments indicating characters or digits, while the scale display panel 23 includes a scale section 23a (FIG. 4) formed of a multitude of LED's arranged in a row and over scale indicators 23b arranged at both ends of the scale section 23a. These display panels 22 and 23 are connected to connector pins 26 and 27 by means of signal lines 24 and 25, respectively.

In a light supply unit 31 to which the connector 11a of the endoscope 11, there are provided a transmitter 32 supplying drive pulses to the ultrasonic transducer 17 and a receiver 33 receiving echo signals from the ultrasonic transducer 17. The output terminal of the receiver 33 is connected to the reset terminal of a time counter 35 through an amplifier 34. The set terminal of the time counter 35 is connected with the output terminal of the transducer 32. The output terminal of the time counter 35 is connected to the input terminal of a distance calculator 36. The output terminal of the distance calculator 36 is connected to one input terminal of a scale calculator 37 and to a decoder/driver 38. The other input terminal of the scale calculator 37 is connected with a view angle data circuit 39, and the output terminal of the calculator 37 is connected to the input terminal of a decoder/driver 40. The output terminals of the decorder/drivers 38 and 40 are connected to the connector pins 26 and 27, respectively. A light source 41 is disposed in the light supply unit 31 so as to face the incidence-side ends of the light guides 12, and is supplied with electric power by a power source 42.

In the above-mentioned endoscope apparatus, when an insertion section 11c of the enddoscope 11 is inserted into e.g. a body cavity and the power supply is put to work, the transmitter 32 produces drive pulses, which are supplied to the ultrasonic transducer 17 through the connector pin 19 and the signal line 18. The ultrasonic transducer 17 produces an ultrasonic wave in response to the drive pulse. In response to the drive pulse, moreover, the time counter 35 is set. The ultrasonic wave is reflected by a subject 28, and reflected waves or echo waves are projected on the ultrasonic transducer 17. The echo waves are converted by the ultrasonic transducer 17 into an echo signal, which is applied to the receiver 33 through the signal line 18 and the connector pin 17. The receiver 33 shapes the waveform of the echo signal and applies it to the amplifier 34. The echo signal amplified by the amplifier 34 is applied to the reset terminal of the time counter 35 to reset the same. The time counter 35 starts a time count in response to the drive pulse and stops it in response to the echo signal, thus counting the time T between the transmission of the ultrasonic wave and reception of the ultrasonic echo waves. When the time data T from the time counter 35 is applied to the distance calculator 36, the distance calculator 36 calculates the distance D between the distal end of the endoscope 11 and the subject 28 on the basis of the time data T. This distance D can easily be calculated in accordance with the velocity propagation and transmission/reception time of the ultrasonic waves. The ultrasonic wave propagation velocity V is constant, and the transmission-to-reception time T of the ultrasonic wave is measured in time counter 35. As is known, the distance D is defined by $D = V \times T/2$. When the distance data D is applied to the decoder/driver 38, it is converted into, for example, a 7-segment signal and applied through the connector pin 26 and the signal line 24 to the display panel 22 to be indicated thereon. The distance data D is supplied to the scale calculator 37 which calculates a scale on the basis of the distance D data from the distance calculator 36 and view angle data from the view angle data circuit 39. The view angle is determined by the focal length and the characteristics of lens 14, which is known. In the scale calculator 37, the ratio $L_S/L_I$ of the subject size $L_S$ to the image size $L_I$ in the field of view, i.e. the magnification of the image, is calculated in accordance with the distance data (derived from distance calculator 36) and view angle data, i.e. the magnification of the objective lens (which is known). In another example, the field image is half the size of the subject, for example, a scale "½" will be delivered as the scale information. When this scale information is transferred to the decoder/driver 40, the decoder/driver 40 delivers a display drive signal corresponding to the scale information. When the display drive signal is supplied to the scale display panel 23, a unit scale interval corresponding to the scale information is displayed on the scale display panel 23. Namely, where the given scale information is "½", the LED's of the scale section 23a glows to indicate 10 mm if the image in the field of view measures 5 mm. Information regarding the size of the affected part is displayed according to the scale of the scale section 23a. If the scale information is such that the unit scale interval is greater than the length of the scale section 23a, then the over scale indicators 23b will be lighted.

Figure 5:
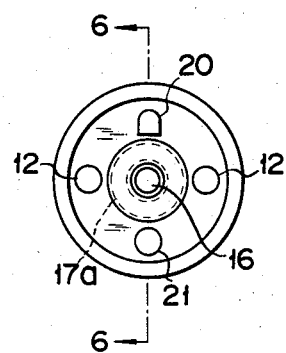
FIG. 5 is a plan view of the distal end portion of an endoscope apparatus according to another embodiment of the invention.
Figure 6:
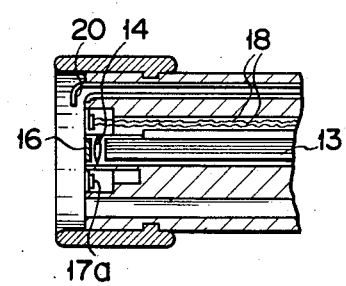
FIG. 6 is a sectional view taken along line 6—6 of FIG. 5.

In the above embodiment, the ultrasonic transducer is disposed in close vicinity to the observation window 16. Alternatively, however, there may be used a ring-shaped ultrasonic transducer 17a which concentrically surrounds the observation window 16, as shown in FIGS. 5 and 6. According to this embodiment, an ultrasonic wave transmitted from the ultrasonic transducer 17a advance and are reflected concentrically with the center of the observation window 16 or the optical axis of the image guide, so that there will be caused no deviation between the optical axis and the transmission axis of the ultrasonic wave. Thus, the accuracy in the distance measurement is improved to ensure accurate scale display, as well as improved accuracy in size measurement.

According to this invention, as described above, there is provided an endoscope apparatus in which an ultrasonic transducer is disposed at the distal end of an endoscope, the ultrasonic wave transmission/reception time of the ultrasonic transducer is measured, and a scale corresponding to the size of a subject image in an optical system for observation of the endoscope is calculated on the basis of the transmission/reception time and the view angle of the optical system, and is displayed on a scale display panel inside the field of view of the optical system. More specifically, length corresponding to the unit scale, which appears in the view field, is calculated on the basis of the transmission-to-reception time interval, as well as the angle of view and effective diameter of the observation optical system, which depend on the kind of the endoscope, and is displayed in the view field together with the object under observation. Thus, the size of a subject, such as an affected part of the body wall, can be measured accurately. In particular, the distance between the distal end of the endoscope and the subject is measured on the basis of the ultrasonic transmission/reception time, and the division of the scale depends on such distance, so that the scale is considerably high in accuracy. Since the scale display, moreover, is performed fully automatically, the endoscope can be operated with ease.

In the above-mentioned embodiments, the scale display panel is formed of LED's. Alternatively, however, the scale display panel may be formed of an LCD (liquid crystal display) having a plurality of electrodes corresponding to the division of the scale, or of any other suitable electrical or mechanical elements. Further, the distance display panel is not essential. Furthermore, the circuits for calculating the scale and the like need not always be provided in the light supply unit, and may alternatively be disposed in the endoscope, for example.

What is claimed is:

1. An endoscope apparatus comprising:
an endoscope including an observation optical system having an eyepiece section and an image guide means and objective lens system for guiding an image of a subject to said eyepiece section so that the image is observed at the eyepiece section; a light guiding optical system having light guide means for guiding illumination light for illuminating the subject; an insertion section having a distal end portion; at least one ultrasonic transducer disposed at said distal end portion of said insertion section for transmitting and receiving ultrasonic waves to and from the subject; and display means disposed inside a field of view of said observation optical system and displaying at least one scale the graduation of which is variable;

distance information output means including means for measuring the time between the transmission of the ultrasonic waves and the reception of the ultrasonic waves reflected from said subject; means for calculating a distance between said distal end portion of said insertion section and the subject as a function of at least said measured time and a velocity of propagation of the ultrasonic waves; and means coupled to the calculating means for generating distance information representing the distance calculated;

view angle information supplying means for supplying at least view angle information representing an angle-of-view of said observation optical system; and circuit means coupled to said distance information output means and to said view angle information supplying means and including:

means for calculating a ratio of the size of an image observed in said field of view of said optical system to the size of the subject, said ratio being calculated on the basis of at least said distance information generated by said distance information output means and said view angle information supplied from said view angle information delivering means; and means for calculating an actual distance scale as a function of said calculated ratio and unit scale information; and means for setting the graduations of said display means to display set graduations in accordance with said actual distance scale.

2. An endoscope apparatus according to claim 1, wherein said display means comprises a plurality of light emitting diodes arranged in a row, said light emitting diodes emitting light with every unit scale interval in accordance with said calculated ratio.

3. An endoscope apparatus according to claim 1, wherein said display means comprises a liquid crystal display having a plurality of electrodes corresponding to divisions of said scale, said liquid crystal display displaying said scale at unit scale intervals in accordance with said calculated ratio.

4. An endoscope apparatus according to claim 1, wherein said observation optical system has an optical axis, and wherein said ultrasonic transducer is disposed in close proximity to said optical axis of said observation optical system.

5. An endoscope apparatus according to claim 1, wherein said observation optical system has an optical axis, and wherein said ultrasonic transducer is a ring-shaped ultrasonic transducer disposed concentrically with, and in close proximity to, said optical axis of said observation optical system.

6. An endoscope apparatus according to claim 1, wherein said display means includes a distance display panel for displaying distance.

7. An endoscope apparatus according to claim 1, wherein said distance information output means includes:

a time counter set to count time in response to the ultrasonic transmission of said ultrasonic transducer and reset in response to the reception of said reflected ultrasonic wave; and a calculator coupled to said time counter for calculating said measured time as a function of the output of said time counter and of the velocity of propagation of said ultrasonic wave.

8. An endoscope apparatus according to claim 2, wherein said observation optical system has an optical axis, and wherein said ultrasonic transducer is disposed in close proximity to said optical axis of said observation optical system.

9. An endoscope apparatus according to claim 3, wherein said observation optical system has an optical axis, and wherein said ultrasonic transducer is disposed in close proximity to said optical axis of said observation optical system.

10. An endoscope apparatus according to claim 4, wherein said distance information output means includes:

a time counter set to count time in response to the ultrasonic transmission of said ultrasonic transducer and reset in response to the reception of said reflected ultrasonic wave; and a calculator coupled to said time counter for calculating said measured time as a function of the output of said time counter and of the velocity of propagation of said ultrasonic wave.

* * * * *